United States Patent
Yamamoto et al.

(10) Patent No.: US 7,072,700 B2
(45) Date of Patent: Jul. 4, 2006

(54) BIOLOGICAL PHOTOMETRIC DEVICE

(75) Inventors: Tsuyoshi Yamamoto, Kawagoe (JP); Atsushi Maki, London (GB); Hideaki Koizumi, Tokyo (JP); Fumio Kawaguchi, Hinode (JP); Michiyuki Fujiwara, Kashiwa (JP); Mikihiro Kaga, Abiko (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/148,991

(22) PCT Filed: Nov. 29, 2000

(86) PCT No.: PCT/JP00/08425

§ 371 (c)(1),
(2), (4) Date: Sep. 9, 2002

(87) PCT Pub. No.: WO01/47422

PCT Pub. Date: Jul. 5, 2001

(65) Prior Publication Data
US 2003/0088162 A1 May 8, 2003

(30) Foreign Application Priority Data
Dec. 27, 1999 (JP) .................. 11-368620

(51) Int. Cl.
*A61B 5/00* (2006.01)
(52) U.S. Cl. .................... 600/310; 600/473; 600/476
(58) Field of Classification Search ........... 600/309, 600/310, 475, 476, 344, 407, 473
See application file for complete search history.

(56) References Cited

U.S. PATENT DOCUMENTS 5,551,422 A 9/1996 Simonsen et al.
(Continued)

FOREIGN PATENT DOCUMENTS

JP 3016160 7/1995
(Continued)

OTHER PUBLICATIONS

Applied Optics, vol. 33, No. 28, Oct. 1994, "Experimental Study of the Effect of Absorbing and Tarnsmitting Inclusions in Highly Scattering Media", N. Bruce, pp. 6692-6698.

*Primary Examiner*—Eric F. Winakur
(74) *Attorney, Agent, or Firm*—Mattingly, Stanger, Malur & Brundidge, P.C.,

(57) ABSTRACT

The invention provides a biological photometric device characterized by a method of disposing a light source and a light detector, capable of measuring a distribution of concentrations at different depths and changes in the concentration in the case of measuring and forming an image of the concentration of metabolites in an organ and changes in the concentration. The light sources and light detectors are disposed on the subject so that, in the case of measuring a concentration of metabolites in an organ and changes in the concentration in a shallow portion in the subject by using an about midpoint position between each of the light sources and each of the light detectors as a sampling point, measurement is performed by using a sampling point of a pair of the light source and said light detector which are disposed at a small interval. In the case of measurement in a deep portion in the subject, a sampling point of a pair of the light source and the light detector which are disposed at a large interval is used.

5 Claims, 13 Drawing Sheets

U.S. PATENT DOCUMENTS

| | | | |
|---|---|---|---|
| 5,676,143 A * | 10/1997 | Simonsen et al. | 600/316 |
| 5,853,370 A | 12/1998 | Chance et al. | |
| 5,902,235 A | 5/1999 | Lewis et al. | |
| 6,016,435 A | 1/2000 | Maruo et al. | |
| 6,032,071 A * | 2/2000 | Binder | 600/476 |
| 6,240,309 B1 | 5/2001 | Yamashita et al. | |
| 6,264,610 B1 * | 7/2001 | Zhu | 600/443 |
| 6,397,099 B1 * | 5/2002 | Chance | 600/473 |
| 2002/0019587 A1 * | 2/2002 | Cheng et al. | 600/322 |

FOREIGN PATENT DOCUMENTS

| | | | |
|---|---|---|---|
| JP | 9-98972 | | 4/1997 |
| JP | 9-135825 | | 5/1997 |
| JP | 10-148611 | | 6/1998 |
| JP | 2000-136997 | | 5/2000 |
| WO | WO97/18755 | * | 5/1997 |

* cited by examiner

| | LIGHT SOURCE | LIGHT DETECTOR |
|---|---|---|
| PAIR 1 | ○ | ● |

|  | LIGHT SOURCE | LIGHT DETECTOR | SAMPLING POINT |
|---|---|---|---|
| PAIR 1 | ○ | ● | ○ |
| PAIR 2 | □ | ■ | ○ |
| PAIR 3 | △ | ▲ | ○ |

BIOLOGICAL PHOTOMETRIC DEVICE

TECHNICAL FIELD

The present invention relates to a biological photometric device and, more particularly, to a biological photometric device for measuring a concentration of metabolites in an organ by using light and changes in the concentration.

BACKGROUND ART

As biological photometric devices for measuring a concentration of metabolites in an organ by using light or changes in the concentration, Japanese Patent Application Laid-Open No. 9-135825 discloses a biological photometric device of high sensitivity in a deep portion in an organ and Japanese Patent Application Laid-Open No. 9-98972 discloses a method of forming an image showing functions of human metabolism by using a measurement result. Prior arts will be described hereinbelow on the basis of the methods.

First, taking a change in blood volume in association with brain functions in the cerebral cortex as an example, a method of non-invasively measuring a change in blood volume in an organ will be described with reference to FIG. 12. A light propagation path 1101 shown in the diagram is a propagation path of light emitted from a light source 1102 and reached a light detector 1103 disposed on a scalp 1107 of a subject 1104. In this case, the light detector includes a light source typified by a laser, a light emitting diode, or a lamp and, in some cases, an optical waveguide for guiding light from the light source to the subject 1104.

As shown in FIG. 12, each of the light source 1102 and the light detector 1103 is fixed to a holder 1105 by using a screw 1106. The tip of each of the light source 1102 and the light detector 1103 is in contact with the scalp. The brain is constructed by, in accordance with the order from the surface of the head with which an optical fiber is in contact, the scalp 1107, a skull 1108, a cerebrospinal layer 1109, a cerebral cortex 1110, and the like.

In the biological photometric device, in the case of measuring, for example, brain functions of an adult, the light sources 1102 and the light detectors 1103 are disposed at intervals of 30 mm. The disposition intervals are not limited to 30 mm but are determined in accordance with the structure of brain and optical properties (such as an absorption coefficient and a scattering coefficient) of cerebral substances. The cerebral cortex 1110 is a tissue existing on the inside of the skull and it is known that the cerebral cortex 1110 exists in a region at a depth of about 10 to 15 mm from the scalp in the case of an adult. It is known that the blood volume in the cerebral cortex changes in association with activities of the brain.

As shown by the light propagation path 1101 having the shape of a banana shown in FIG. 12, in the case of setting the disposition interval between the light source and the light detector to 30 mm and detecting a change in blood volume in the cerebral cortex, the sensitivity is the maximum in an about midpoint position between the light source and light detector in the diagram. In the position, according to a simulation of transmission of light in an organ, a light beam becomes the maximum at a midpoint between the light source and light detector. This point is therefore designated as a blood volume change estimating and measuring position. Based on a change in the light amount detected by the light source before and after the blood volume changes, a change in blood volume in the blood volume change estimating and measuring position can be estimated. An example of a method of evaluating a blood volume change is described in detail in Japanese Patent Application Laid-Open No. 9-98972.

A method of forming an image showing the functions of an organ from the result of measurement of the blood volume change will now be described by referring to FIG. 13. Shown in FIG. 13 are: a subject 1201; a measurement area 1202 on the subject; light sources 1203, 1204, 1205, 1206, 1207, 1208, 1209, and 1210 such as semiconductor lasers, light emitting diodes, or lamps which are disposed on light irradiation positions (S1, S2, S3, S4, S5, S6, S7, and S8) on the subject (1201); and photoelectric conversion devices 1211, 1212, 1213, 1214, 1215, 1216, and 1218 typified by avalanche photo diodes and photomultiplier tubes. Light that reached light detection positions on the subject indicated by D1 to D8 in the diagram is led to the photoelectric conversion devices via optical fibers for detection. The light irradiation position and the light detection position are determined at an interval of 30 mm in the case of measuring a metabolite in vivo in the cerebral cortex of an adult.

In the diagram, for example, light reaching the light detection position (D5) in the diagram is light emitted from light irradiation positions (S3, S5, S7, and S6). As described by referring to FIG. 12, the blood volume change estimating and measuring position is in an about midpoint of the light irradiation position and the light detection position. In the measuring method shown in FIG. 13, the number of estimation and measurement positions is 24 (blank circles in the diagram). To form an image showing the concentration of metabolites in an organ or a change in the concentration, first, changes in blood volume are obtained in the positions (24 positions). The changes in blood volume are subjected to two-dimensional spline interpolation, thereby estimating a change in blood volume between the measurement positions and an image is formed by using the result.

According to Neil C. Bruce, "Experimental study of the effect of absorbing and transmitting inclusions in highly scattering media", Applied Optics, No. 28, Vol. 33, October, 1994 issued by Optical Society of America, it is understood that in the case where the disposition interval between a light source and a light detector is narrow, a larger amount of information of the surface of a light scatterer can be obtained.

In the above-described biological photometric methods disclosed in Japanese Patent Application Laid-Open Nos. 9-135825 and 9-98972, to detect changes in metabolism of an organ tissue in a deep portion of the organ typified by the cerebral cortex, a plurality of light sources and a plurality of light detectors are disposed on a subject at predetermined intervals, a concentration of metabolites in the organ at a plurality of sampling points existing in midpoints between the light sources and light detectors or changes in the concentration is measured, and an image showing the concentration of metabolites in the organ or the changes in the concentration is formed by using the measurement result. In the prior arts, however, an image of only the concentration of metabolites in an organ in a certain depth or the changes in the concentration is formed.

DISCLOSURE OF THE INVENTION

By paying attention to those points, an object of the invention is to provide a biological photometric device capable of measuring a concentration of metabolites in an organ in a shallow area and a deep area of an organ tissue and changes in the concentration and generating an image showing a result of the measurement.

To achieve the object, according to the invention, light sources and light detectors are two-dimensionally disposed on a subject of an organ in the vertical and lateral directions. To measure a concentration of metabolites in the organ in a shallow portion in the subject and changes in the concentration and form an image, the concentration of metabolites in the organ and changes in the concentration is measured in an about midpoint position of a pair of the light source and the light detector which are disposed at a small interval. To measure a concentration of metabolites in the organ in a deep portion in the subject and changes in the concentration and form an image, the concentration of metabolites in the organ and changes in the concentration is measured in an about midpoint position of a pair of the light source and the light detector which are disposed at a large interval.

According to the configuration of the invention, there is provided a biological photometric device including a plurality of light sources for irradiating an organ with light and a plurality of light detectors for detecting the light emitted from the light sources and propagated through the organ, the light sources and the light detectors being disposed alternately on the organ, the device for measuring a concentration of metabolites in the organ and changes in the concentration by using an about midpoint position between each of the light sources and each of the light detectors as a sampling point on the basis of the signal detected by the light detector, wherein the light sources and the light detectors are disposed so that positions of the light source and the light detector become sampling points.

According to the configuration of the invention, there is provided a biological photometric device including a plurality of light sources for irradiating a subject with light and a plurality of light detectors for detecting the light emitted from the light sources and propagated through the subject, the light sources and light detectors being disposed on the subject, the device for measuring a concentration of metabolites in the subject and changes in the concentration by using an about midpoint position between the light source and the light detector as a sampling point on the basis of a signal detected by the light detectors, wherein another light detector is disposed in an about midpoint position of a first pair of the light source and the light detector, and another light detector is disposed in an about midpoint position of a second pair of the light source and the light detector.

According to the configuration of the invention, there is provided a biological photometric device including a plurality of light sources for irradiating a subject with light and a plurality of light detectors for detecting the light emitted from the light sources and propagated through the subject, the device for measuring a concentration of metabolites in the subject and changes in the concentration by using an about midpoint position between each of the light sources and each of the light detectors as a sampling point on the basis of a signal detected by the light detector, wherein the light sources and the light detectors in a plurality of pairs are disposed symmetrically so that sampling points in the plurality of pairs of the light sources and the light detectors, of which intervals are different from each other are in the same position in the depth direction.

According to the configuration of the invention, there is provided a biological photometric device including a plurality of light sources for irradiating a subject with light and a plurality of light detectors for detecting the light emitted from the light sources and propagated through the subject, the light sources and the light detectors being disposed alternately in the vertical and lateral directions on the subject, the device for measuring a concentration of metabolites in the subject and changes in the concentration by using an about midpoint position between each of the light sources and each of the light detectors as a sampling point on the basis of the signal detected by the light detector, wherein the light sources and said light detectors are disposed so that a position interval between the light source and the light detector disposed in said lateral direction and a position interval between the light source and the light detector disposed in the vertical direction are different from each other.

Further, the invention further provides a biological photometric device obtained by further providing the configuration with means for displaying the measured concentration of metabolites or changes in the concentration as an image.

BEST MODE FOR CARRYING OUT THE INVENTION

Embodiments of the invention will be described hereinbelow with reference to the drawings.

Figure 1:
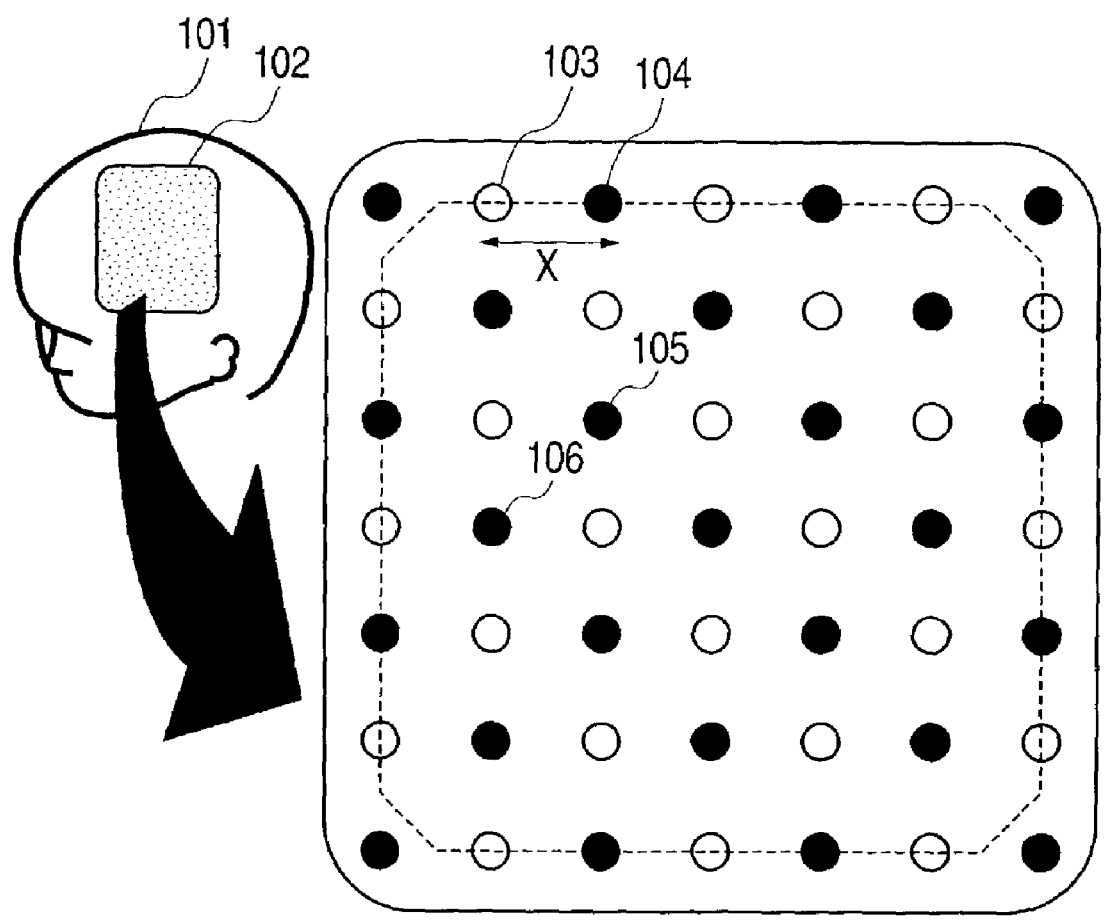
FIG. 1 is a diagram showing a first example of a layout of light sources and light detectors according to the invention.

FIG. 1 shows an example of a method of disposing light sources and light detectors on a subject in accordance with the invention in a biological photometric device.

The light source denotes here a device having a light source typified by a laser, LED, or lamp and light guiding means typified by an optical fiber capable of guiding light emitted from the light source onto a subject. There is no problem that the light sources are directly disposed on a subject. On the other hand, the light detector is a device having a component of detecting light propagated through the subject and converting the detected light amount into an electric signal. As an example of the component, an avalanche photo diode and a photomultiplier tube can be mentioned. Reference numeral 101 in FIG. 1 denotes a subject, and the concentration of metabolites in an organ in the subject in a measurement area (102) existing on the subject or changes in the concentration is/are measured.

The method of disposing the light sources and light detectors on the subject will be described hereinbelow. Blank circles 103 in the diagram denote light sources. On the other hand, painted circles 104 denote light detectors. The disposing interval of them is arbitrary. Means for obtaining an image showing a concentration of metabolites in a shallow area of an organ or changes in the concentration and obtaining an image showing a concentration of metabolites in a deep area in the organ or changes in the concentration by using the method of disposing the light source and light detector shown in FIG. 1 will be described hereinbelow with reference to FIG. 2.

Figure 2:
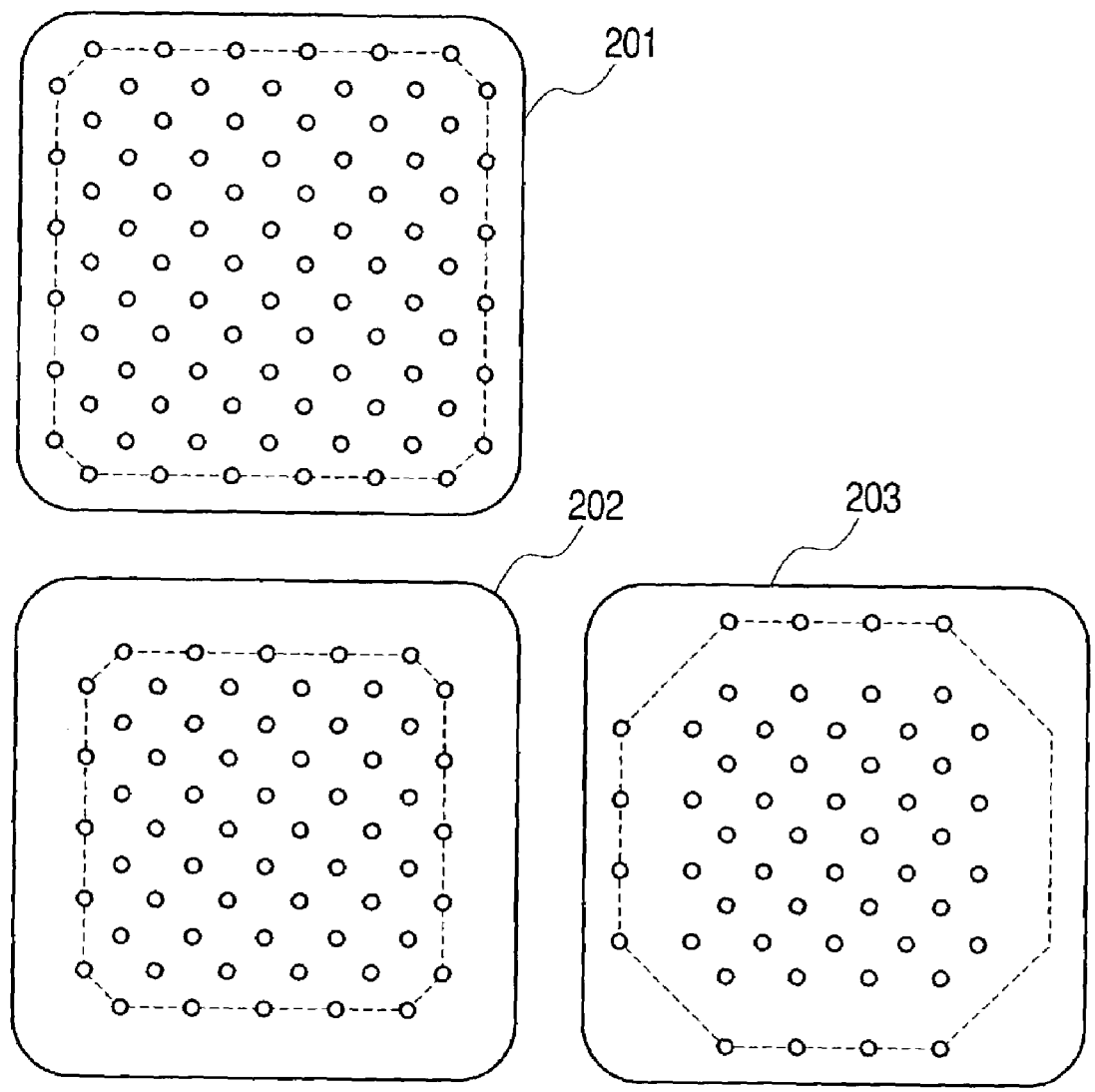
FIG. 2 is a diagram showing a distribution of sampling points and measurement areas in FIG. 1.

201 in FIG. 2 denotes a distribution of sampling points for obtaining an image illustrating the concentration of metabolites in a shallow area of an organ or changes in the concentration by using the method of disposing the light sources and light detectors shown in FIG. 1. In FIG. 1, for example, the interval (which is designated as "x") between the light source 103 and the light detector 104 is the shortest. Consequently, the concentration of metabolites in an organ at a sampling point existing in an about midpoint position of the light source and light detector or changes in the concentration indicates a concentration in a shallowest area in the organ or changes in concentration. A dotted line shown in 201 indicates a measurement area obtained by surrounding sampling points at about midpoint positions of the light sources and light detectors disposed at the disposing intervals "x". An image of the concentration of metabolites in an organ in the area or the changes in the concentration is formed by using a mathematical processing method typified by spline interpolation.

A method of forming an image showing a concentration of metabolites in an organ in a deeper area or changes in the concentration in a similar manner will be described by using 202 and 203 in FIG. 2. 202 indicates a distribution of sampling points in the case of forming an image showing a concentration of metabolites in an organ in about midpoint positions between the light sources 103 and light detectors 105 shown in FIG. 1 (in this case, the interval between the light source and the light detector is 2.23x) or changes in the concentration. Further, 203 denotes a distribution of sampling points in the case of forming an image showing a concentration of metabolites in an organ in about midpoint positions between the light sources 103 and the light detectors 106 shown in FIG. 1 (in this case, the interval between the light source and the light detector is 3x) or changes in the concentration.

As described above, the narrower the disposing interval between the light source and light detector is, a larger amount of information of the surface of light scatterer can be obtained. Consequently, it can be said that 202 shows a distribution of sampling points by which the concentration of metabolites in a deeper area of an organ or changes in the concentration can be detected as compared with the distribution 201, and that 203 indicates a distribution of sampling points in a deeper area as compared with 201 and 202. From the above, each of images obtained by performing a mathematical process on the concentration of metabolites in an organ at the sampling points or changes in the concentration displays a distribution of concentrations of metabolites in an organ at a certain depth in an organ or changes in the concentration.

Figure 3:
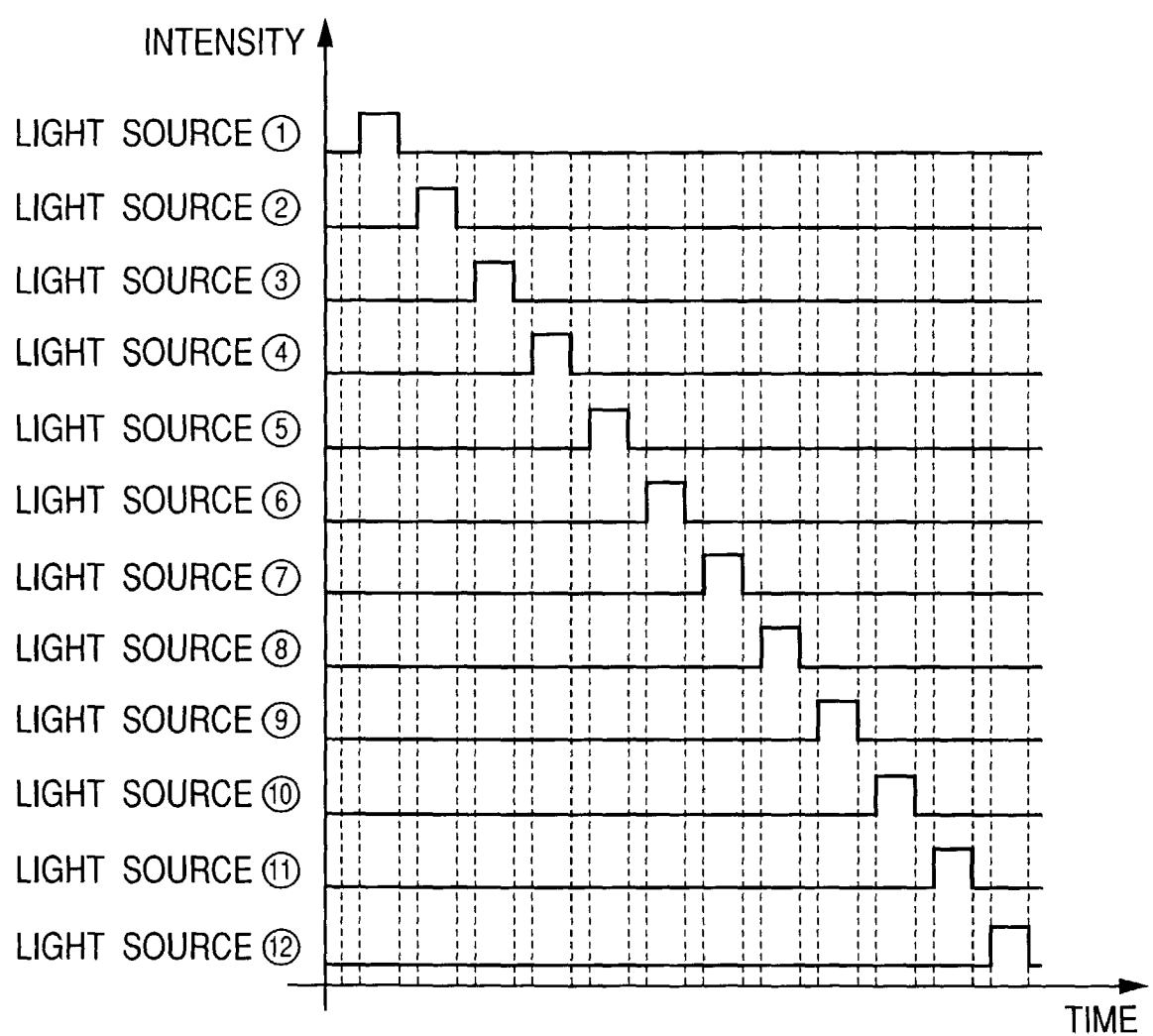
FIG. 3 is a diagram showing an example of a measurement sequence.

FIG. 3 shows an example of a measurement sequence used to measure the concentration of metabolites in an organ or changes in the concentration by using the method of disposing a light source and a light detector shown in FIG. 1. For example, "a light source 1" shown in FIG. 3 corresponds to the light source 103 in FIG. 1. At this time, as shown in FIG. 3, all of the other light sources (light sources 2 to 12 in FIG. 3) are off. After the switch of the light source 1 is turned off, the intensity of the light source 2 is turned on. The time elapsed since the switch of the light source 1 is turned off until the switch of the light source 2 is turned on largely depends on time required to detect a light amount by a detector and convert the light amount to an electric signal and a time constant of an electronic circuit after the light amount is converted into the electric signal. After that, the switches are sequentially turned on or off from the light source 2 to irradiate the subject with light.

Figure 4:
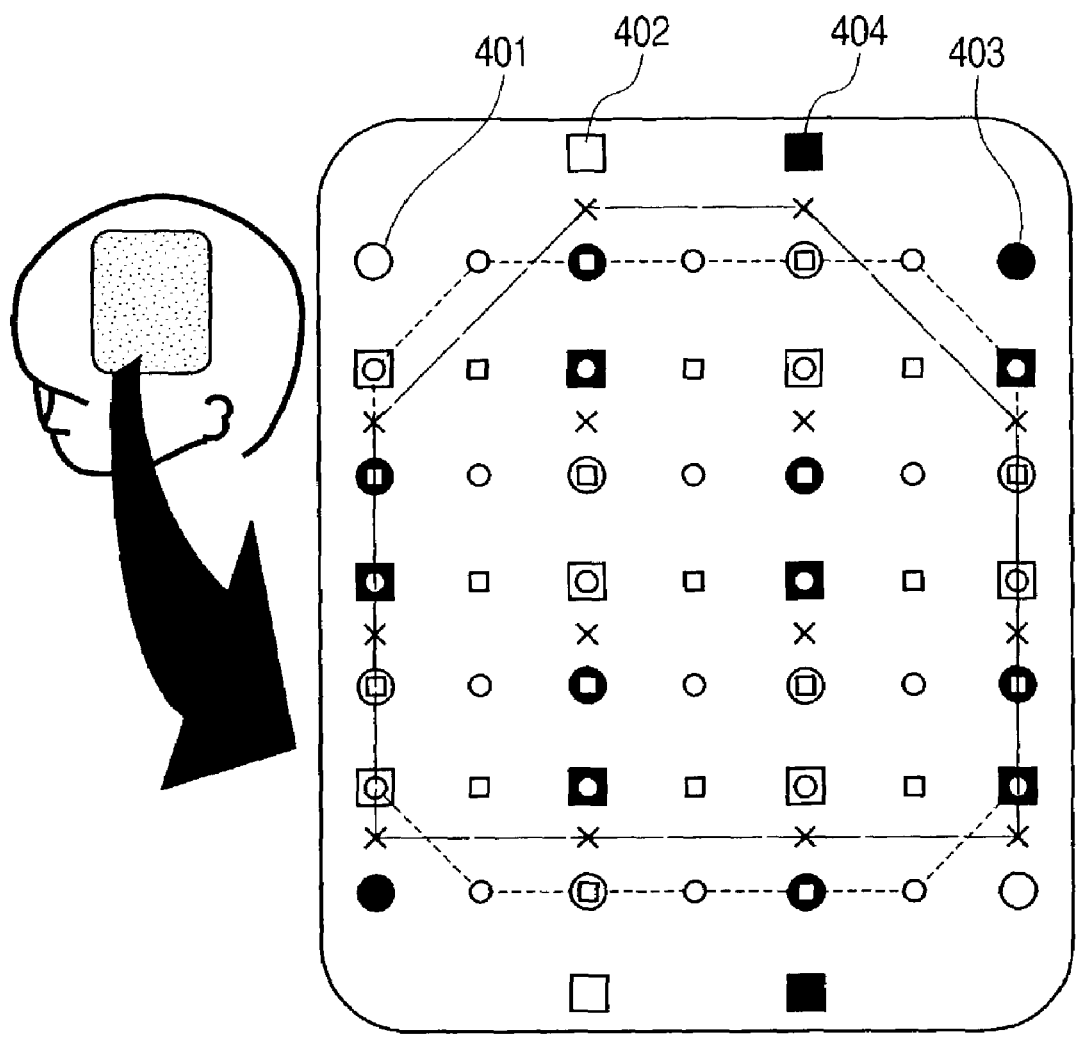
FIG. 4 is a diagram showing a second example of the layout of light sources and light detectors according to the invention.

In the method of disposing the light sources and the light detectors shown in FIG. 1, the light sources and light detectors are alternately disposed on a two-dimensional plane. FIG. 4 shows an example of a disposing method different from the above method. Blank circles 401 and blank squares 402 in the diagram denote light sources, and painted circles 403 and painted squares 404 indicate light detectors. In the diagram, the light sources shown by blank circles and the light detectors shown by painted circles are disposed at the equal intervals, and the light sources indicated by blank squares and the light detectors indicated by painted squares are disposed at the equal intervals.

In the method of disposing the light sources and light detectors shown in FIG. 4, at least four pairs of the light sources and light detectors which will be described hereinbelow can be considered.

A first pair is a pair of the light source indicated by the blank circle for emitting light and the light detector indicated by the painted circle for detecting the light propagated through an organ tissue. Sampling points as midpoints of the light sources and light detectors are indicated by small blank circles in the diagram. Similarly, a second pair is a pair of the light source indicated by the blank square for emitting light and the light detector indicated by the painted square for detecting the light propagated through the organ tissue, and sampling points are shown by small blank squares.

In contrast to the first and second pairs, in third and fourth pairs, light emitted from the light sources shown by the blank squares and blank circles and propagated through an organ tissue is detected by the light detectors of the painted circles and painted squares. Consequently, in the configuration, in an about midpoint position in a pair of a light source and a light detector, another light source or light detector is disposed. In this case, the interval of the light source and light detector is the half of the interval between the light source and light detector shown in the first and second pairs, and sampling points obtained from the third and fourth pairs are indicated by the sign "x".

Figure 5:
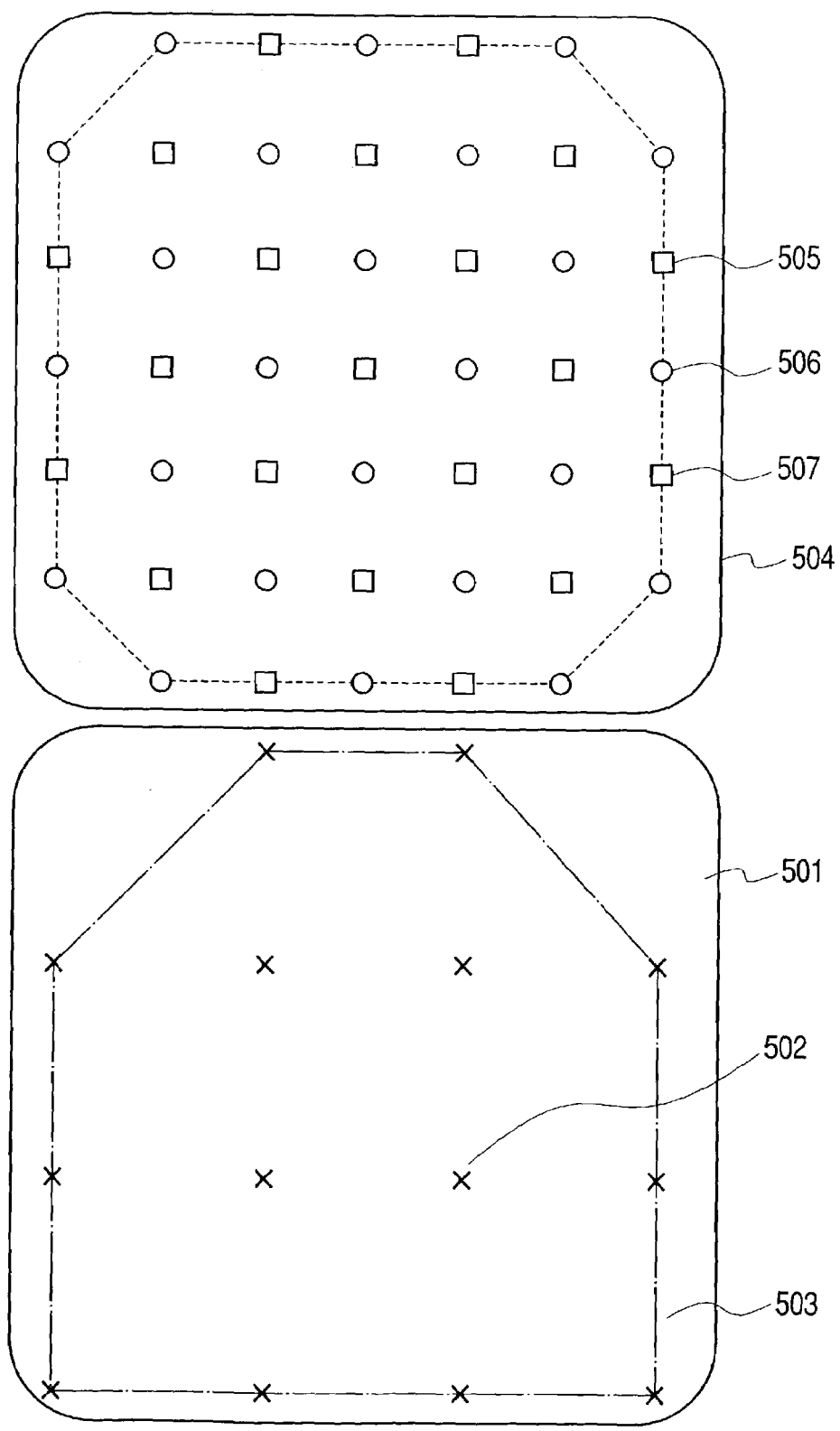
FIG. 5 is a diagram showing a distribution of sampling points and measurement areas in FIG. 4.

FIG. 5 shows a distribution of sampling points obtained from the method of disposing the light sources and light detectors illustrated in FIG. 4. 501 shows a distribution of sampling points 502 obtained by the third and fourth pairs shown in FIG. 4 and an area 503 of the sampling points. Similarly, 504 shows a distribution of sampling points 505 and 506 obtained by the first and second methods of disposing the light sources and light detectors shown in FIG. 4 and an area 507 of the sampling points. As compared with the first and second pairs shown in FIG. 4, in the third and fourth pairs, the disposition interval of the light source and the light detector is narrower. Therefore, a distribution of an image obtained by interpolating the distribution 501 of the sampling points obtained by the latter pairs shows a shallower area of the subject as compared with a distribution of an image obtained by the former pairs.

In the methods of disposing the light sources and light detectors shown in FIGS. 1 and 4, the light sources and light detectors are uniformly disposed in the measurement area. As a result, in a shallow area and a deep area of the subject, images of almost the same measurement areas can be formed. However, depending on an object to be measured, there is a case such that depth information regarding a metabolite in an organ of the subject only in a specific area is necessary.

Figure 6:
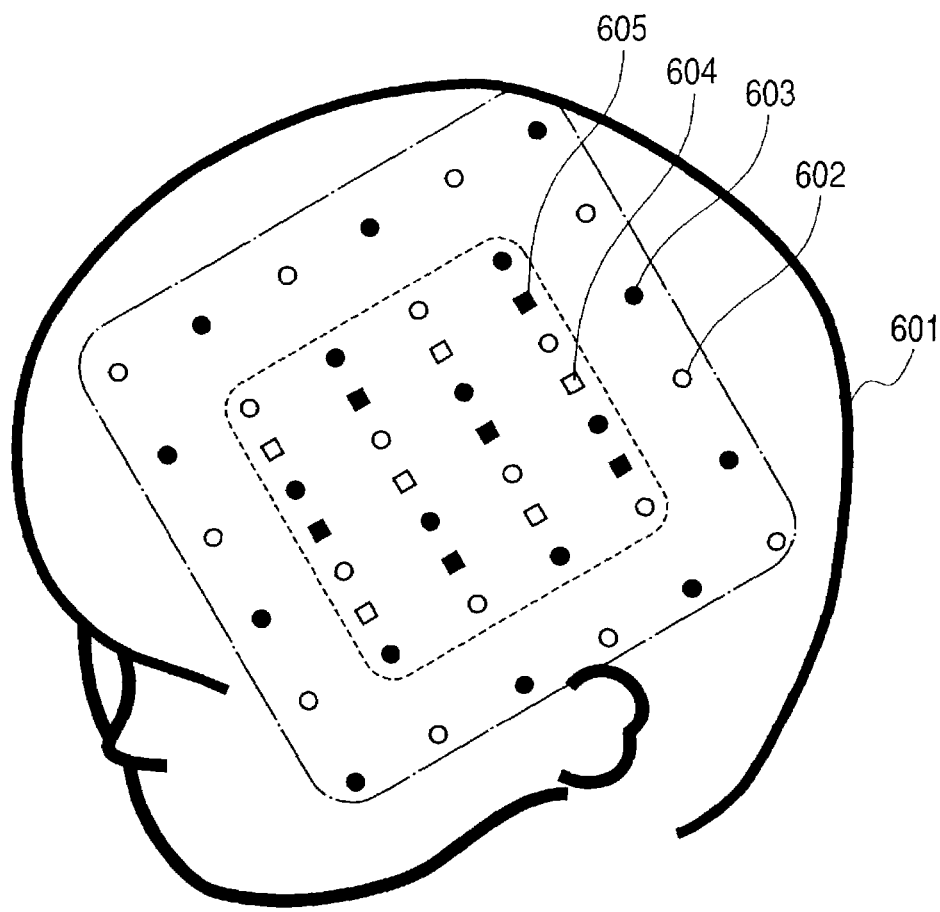
FIG. 6 is a diagram showing a third example of the layout of light sources and light detectors in the invention.

FIG. 6 shows an example of a method of disposing light sources and light detectors, capable of achieving the object. In the measurement method, light sources (602) indicated by blank circles and light detectors (603) indicated by painted circles are disposed on the whole face of a subject 601. On the other hand, light sources (604) indicated by blank squares and light detectors (605) indicated by painted squares are locally disposed on the subject 601.

Figure 7:
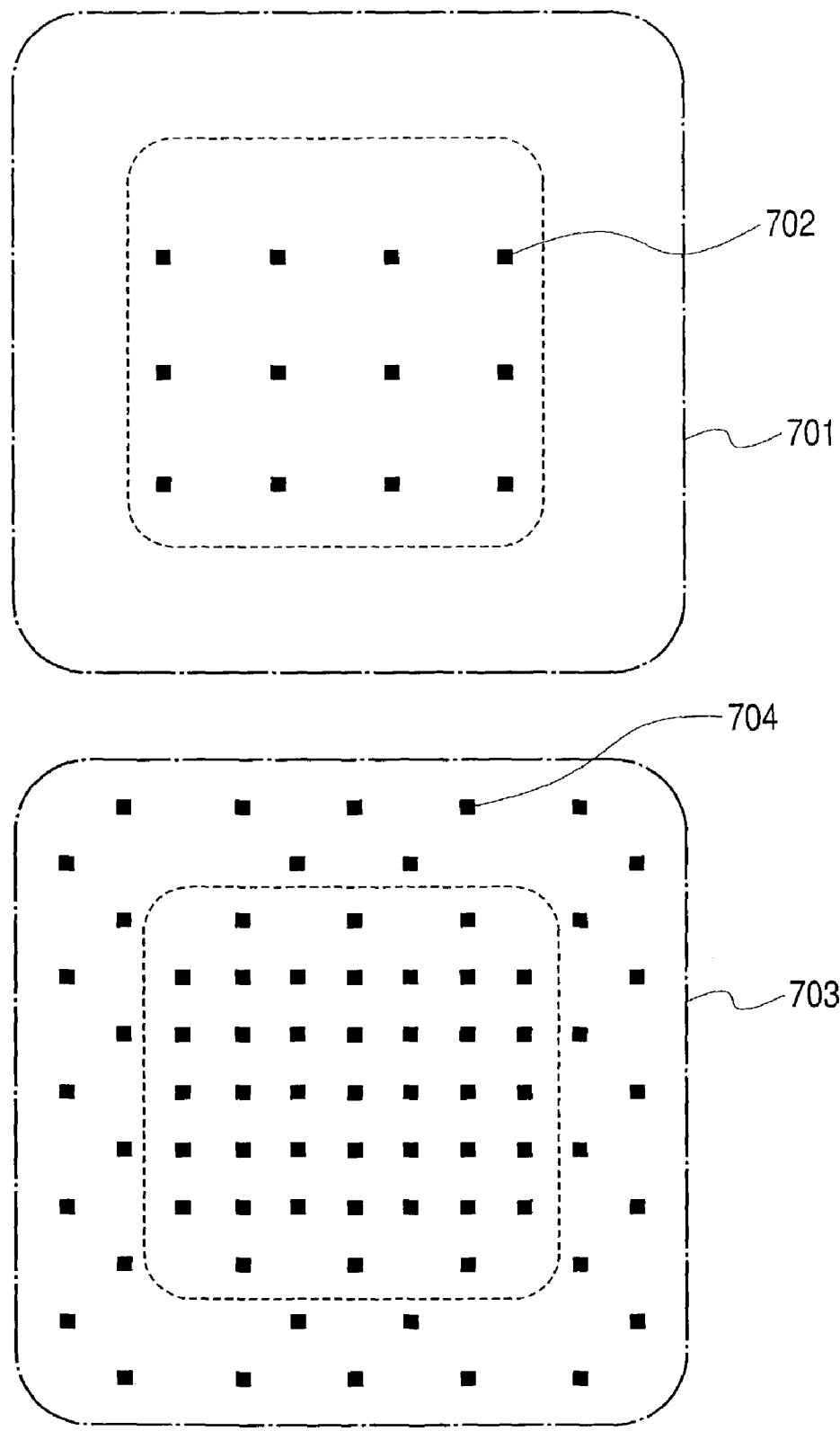
FIG. 7 is a diagram showing a distribution of sampling points and measurement areas in FIG. 6.

In the method of disposing the light sources and light detectors shown in FIG. 6, FIG. 7 shows a distribution of sampling points. 701 denotes a distribution of sampling points 702 existing in about midpoint positions of the light sources and light detectors in the pairs 3 and 4 shown in FIG. 6. 703 denotes a distribution of sampling points 704 existing in about midpoint positions of the light sources and light detectors in the pairs 1 and 2 shown in FIG. 6.

In FIG. 6, the disposition interval between the light source and light detector shown in the pairs 1 and 2 is twice as long as that between the light source and light detector shown in the pairs 3 and 4. It can be consequently said that the distribution map 701 of the sampling points shows the concentration of metabolites in an organ in a shallower area of a subject or changes in the concentration as compared with the distribution map 703 of the sampling points. It can be said that the distribution 701 of sampling points is more local as compared with the distribution 703 of sampling points and achieves the above-described object.

Figure 8:
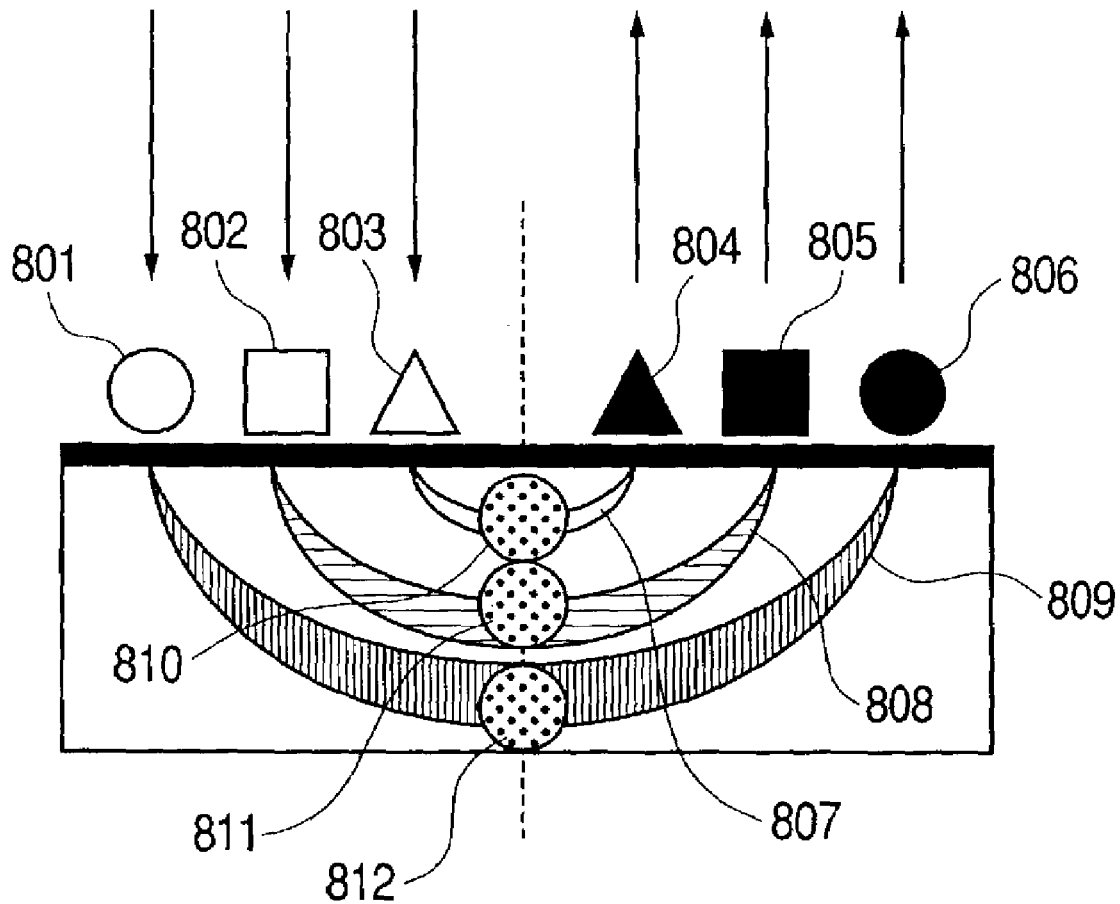
FIG. 8 is a diagram showing a fourth example of the layout of light sources and light detectors according to the invention.

In FIGS. 2, 5, and 7, the positions of sampling points at different depths do not always coincide with each other. FIG. 8 shows an example of a method of disposing light sources and light detectors by which distributions of sampling points at different depths become the same. A blank circle 801, a blank square 802, and a blank triangle 803 in the diagram denote light sources, and light is detected by a painted circle 804, a painted square 805, and a painted triangle 806 shown in the same diagram, respectively. 807, 808, and 809 denote optical path distributions of light emitted from the light sources and reaching the light detectors.

In the method of disposing the light sources and light detectors shown in FIG. 8, the light sources and light detectors are disposed symmetrically. The sensitivity in the midpoint of the light source and the light detector is the highest. As the distance between the light source and the light detector increases, the concentration of metabolites in an organ in deep portions or a change in the concentration can be measured. Consequently, in the measuring method shown in FIG. 8, sampling points 810, 811, and 812 line in the depth direction.

Figure 9:
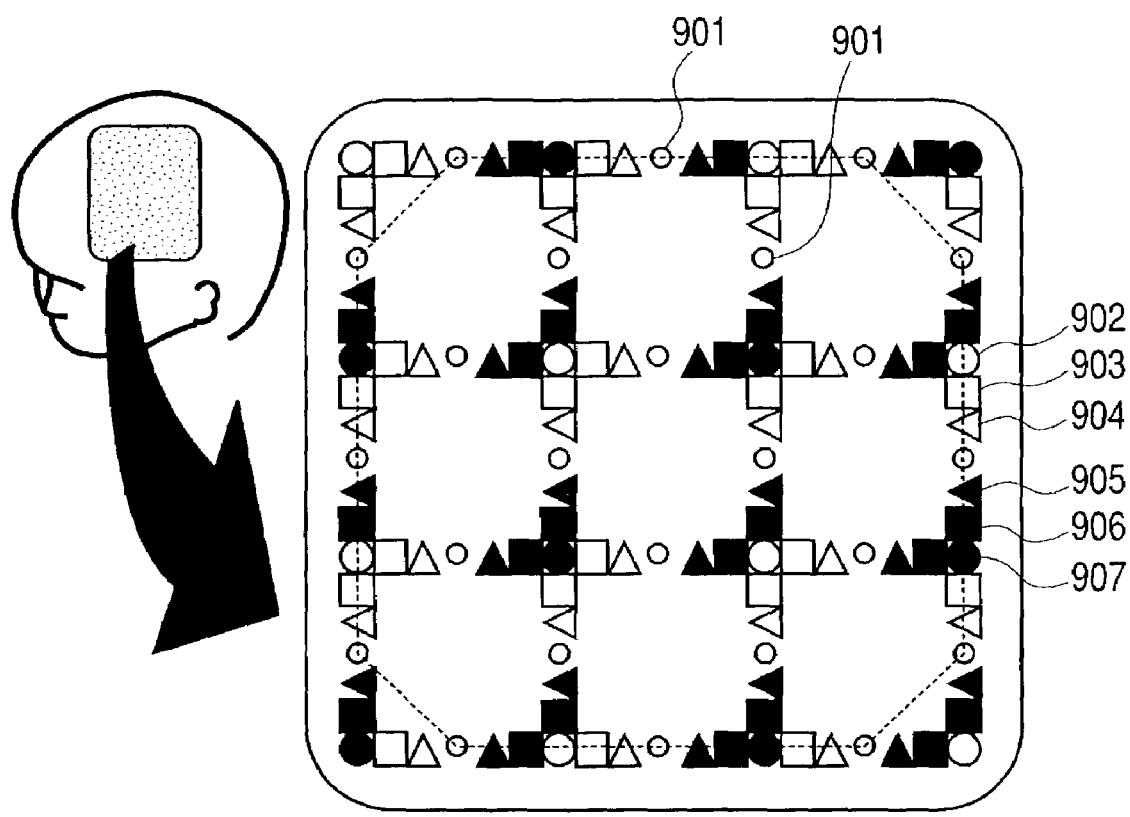
FIG. 9 is a diagram showing an example of the layout of light sources and light detectors in FIG. 8.

FIG. 9 shows a method of disposing a light source and a light detector by which a topographic image in which sampling points exist in the same position in the depth direction can be obtained on the basis of the method of disposing the light source and the light detector shown in FIG. 8. The pairs of the light sources and light detectors are the same as those shown in FIG. 8. In the disposing method, light sources 902, 903, and 904 and light detectors 905, 906, and 907 are disposed line-symmetrically with respect to a sampling point 901 as a center. Therefore, distributions of the sampling points obtained by the pairs 1, 2, and 3 are the same. However, the disposition interval between a light source and a light detector varies according to the pairs. In the case shown in the diagram, the areas in the subject measured become deeper in accordance with the order from the pairs 1, 2, and 3.

Figure 10:
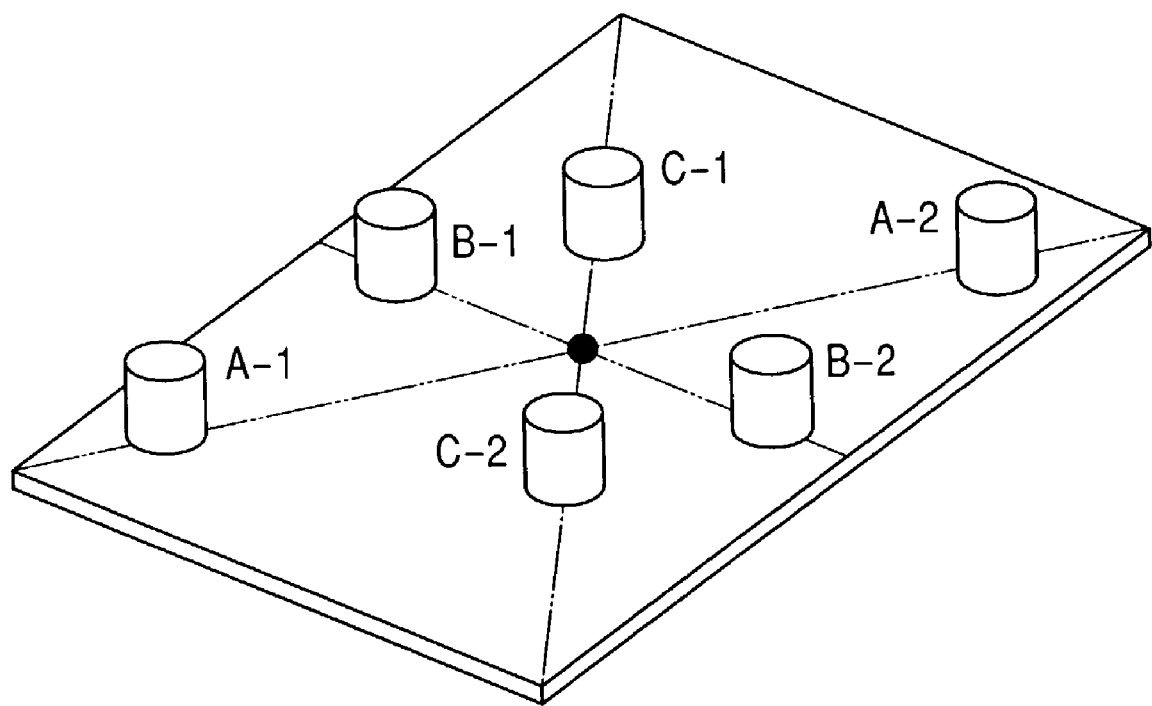
FIG. 10 is a diagram showing a fifth example of the layout of light sources and light detectors in the invention.

Although FIG. 8 shows the configuration of disposing the pairs of light sources and light detectors line-symmetrically and measuring the deep and shallow portions in an organ, the invention is not limited to the configuration but, as shown in FIG. 10, light sources A-1, B-1, and C-1 and light detectors A-2, B-2, and C-2 may be disposed with respect to a sampling point of a change in blood volume indicated by a painted point (painted circle) in the diagram as a center.

In this case, light emitted from the light source A-1 is detected by using the light detector A-2. Similarly, light emitted from the light sources B-1 and C-1 is detected by using the light detectors B-2 and C-2, respectively. In order to extract the information in the shallow portion and the deep portion in more detail, it is necessary to dispose the light sources and light detectors densely. In the disposition configuration of FIG. 8, the disposition is spatially limited. In contrast, by using the embodiment shown in FIG. 10, the disposition of the light sources and light detectors is not so spatially limited, so that information in an organ can be extracted in detail.

An example of displaying a plurality of topographic images measured at different depths onto a screen on the basis of the above-described method will be described. 1001 and 1002 shown in FIG. 11 denote topographic images in a shallow portion and a deep portion obtained by the light sources and light detectors illustrated in FIG. 4.

To obtain the images, images are generated according to an estimating method typified by spline interpolation by using the concentration of metabolites in an organ obtained at different sampling points or changes in the concentration. As indicated by 1005 and 1006, messages indicating the depths at which the images are taken are provided around the images 1001 and 1002. Further, as shown by 1007, it is also possible to obtain a difference between topographic images at different depths and display the difference. In this case, if the topographic image 1007 indicates the difference between the measurement areas 1003 and 1004, a measurement area indicated by 1008 has to be a sum-set of the measurement areas 1003 and 1004.

1009 shows an example of stereoscopically displaying the topographic images in addition to the topographic images 1001 and 1002. In this case, in order to clearly show a geometrical positional relation of topographic images at different depths, a perpendicular 1010 indicative of the positional relation in the vertical direction is added. Although the perpendicular 1010 is a dotted line in the embodiment, it can be a broken line, a solid line, or a thick line.

Figure 11:
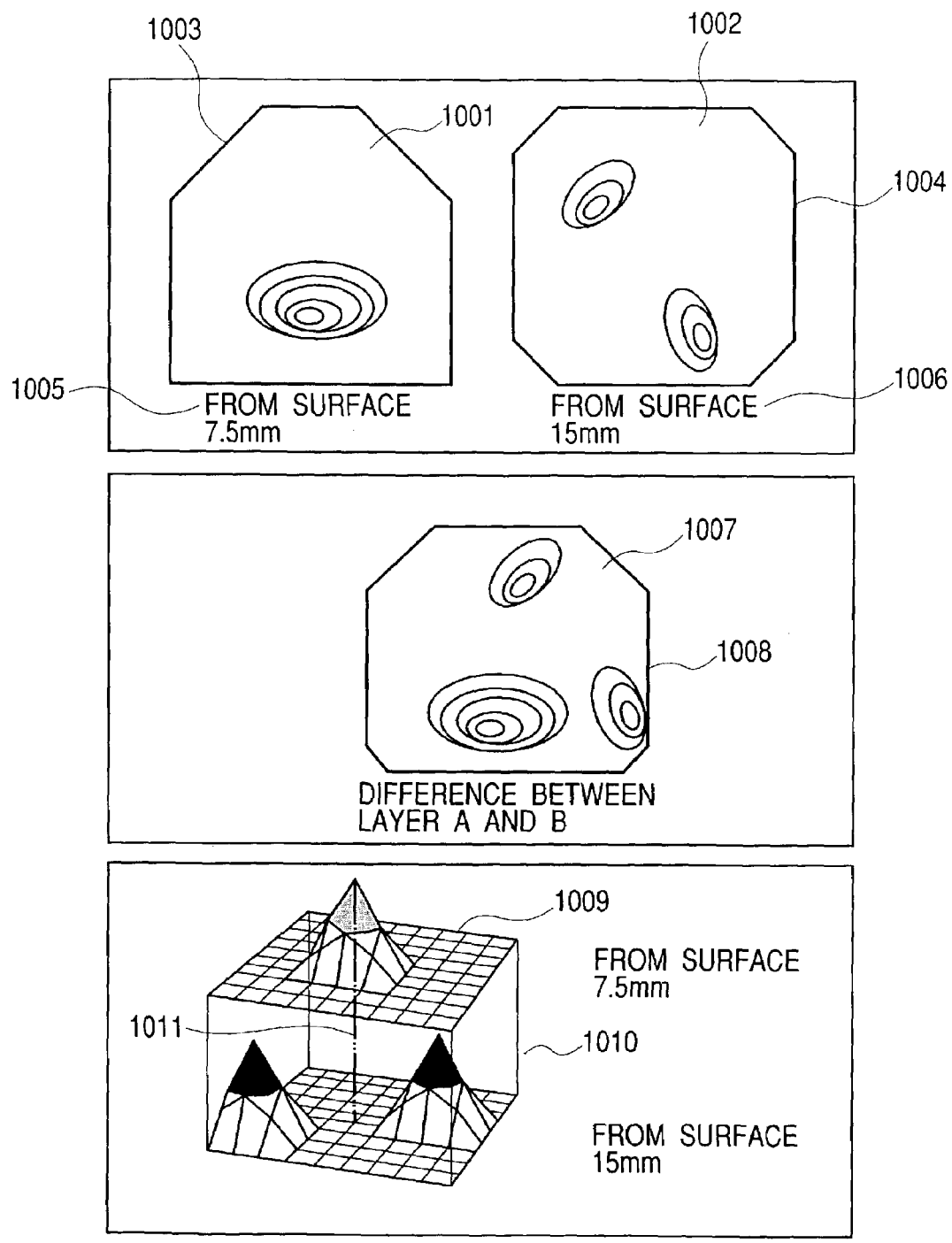
FIG. 11 is a diagram showing an example of a method of displaying a topographic image according to the invention.
Figure 12:
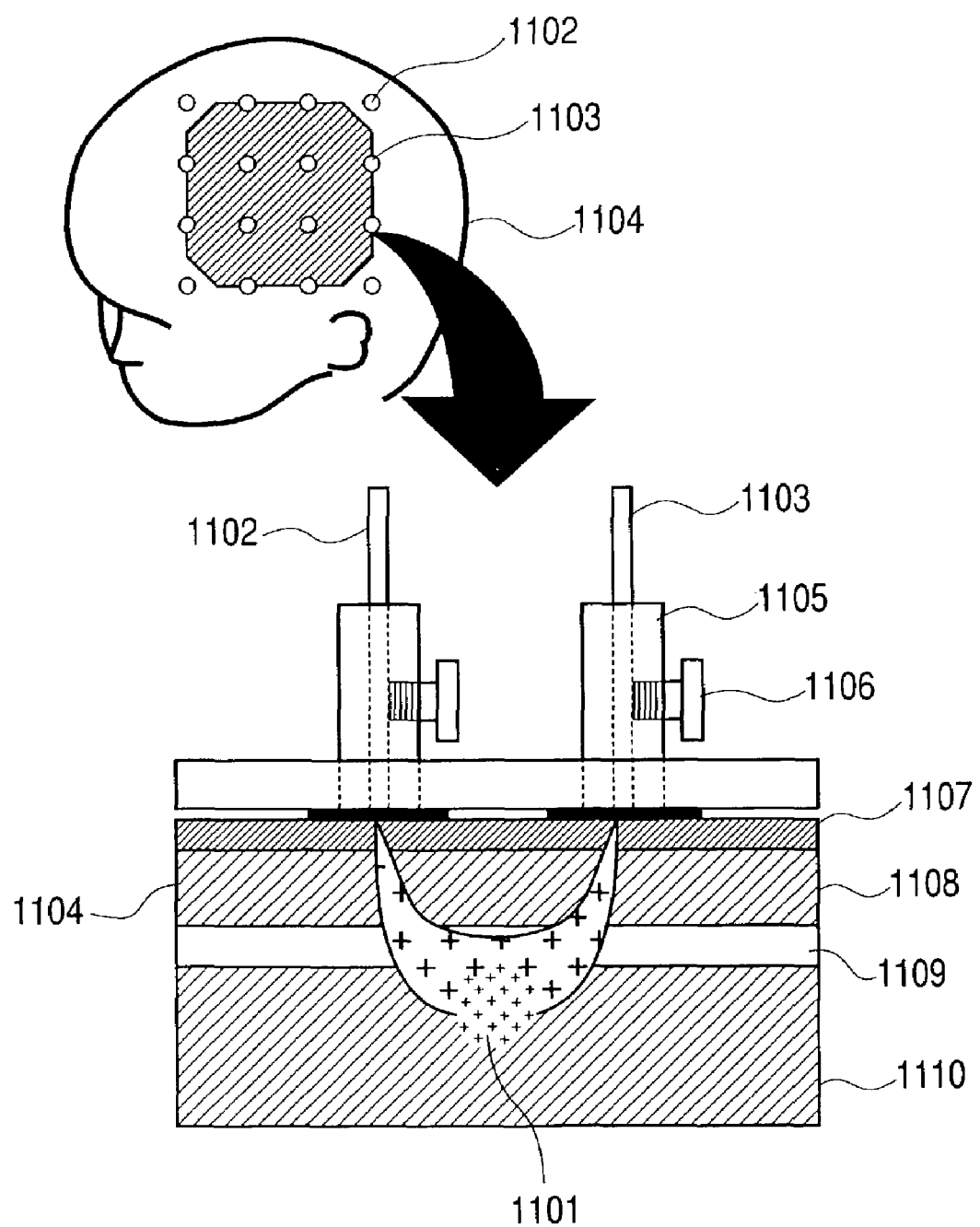
FIG. 12 is a diagram for explaining a conventional method of measuring a concentration of metabolites in an organ by using light or changes in the concentration.
Figure 13:
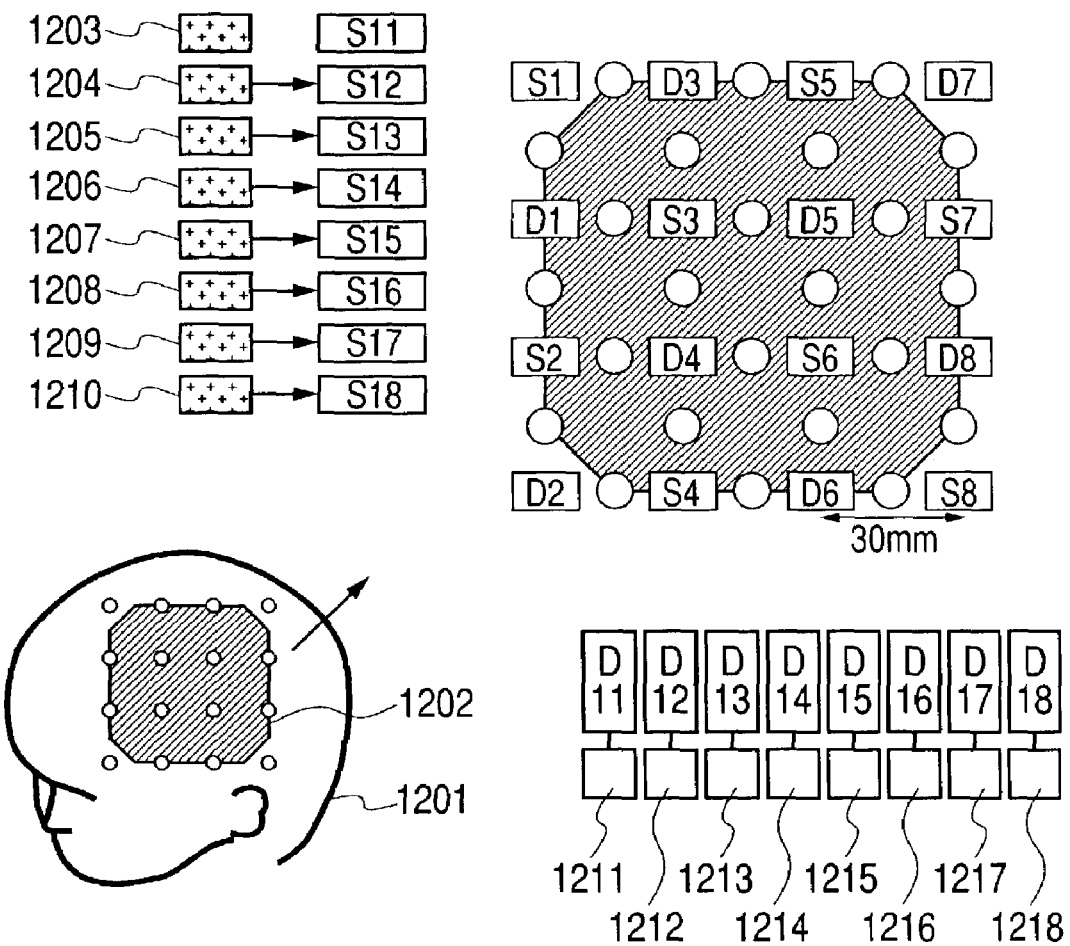
FIG. 13 is a diagram showing a distribution of sampling points in FIG. 12.

A broken line 1011 which is of a kind different from the perpendicular 1010 is used to associate the position in which the concentration of metabolites in an organ in a shallow portion (described as "7.5 mm from the surface" in FIG. 11) or the maximum value of the change in the concentration is obtained with the measurement area in the deep portion (described as "15 mm from the surface" in FIG. 11). The line 1011 is desirably of a kind different from the perpendicular 1010 indicative of the positional relation in the vertical direction, so that the difference becomes clear.

INDUSTRIAL APPLICABILITY

As described above, according to the invention, a biological photometric device capable of measuring a concentration of metabolites in an organ of a subject at different depths from the surface of the subject and changes in the concentration and obtaining it as an image can be realized.

The invention claimed is:

1. A biological photometric device comprising:
an array having a plurality of light sources and corresponding light detectors for respectively irradiating an organ with light and detecting the light emitted from the light sources and propagated through the organ,
the light sources and light detectors adapted to be disposed on the organ including a first light source and a first light detector, and
a device for measuring a concentration of metabolites in the organ and changes in the concentration at a location corresponding to a midpoint position between said first light source and said first light detector as a sampling point,
wherein said light sources and light detectors further include a second light source or a second light detector adapted to be disposed on said sampling point.

2. The biological photometric device according to claim 1, further comprising means for displaying said concentration of metabolites measured or changes in the concentration as an image.

3. The biological photometric device according to claim 1, wherein each of the light sources and each of the light detectors are disposed at intervals of substantially 30 mm.

4. The biological photometric device according to claim 1, further comprising a display to show said concentration of metabolites and changes in the concentration measured as an image.

5. A biological photometric device comprising:
an array having a plurality of light sources and corresponding light detectors for respectively irradiating an organ with light and detecting the light emitted from the light sources and propagated through the organ;
the light sources and light detectors adapted to be disposed on the organ including first, second and third light sources and first, second and third light detectors;
a device for measuring a concentration of metabolites in the organ and changes in the concentration at a location corresponding to a midpoint position between said first light source and said first light detector or between said second light source and said second light detector as a sampling point;
wherein said first light source and said first light detector are on a first line on the organ, and said second light source and said second light detector are on a second line on the organ which is substantially parallel to said first line and a distance between said first line and said second line is substantially the same as a distance between said first light source and said first light detector, and said second light source is at a position substantially nearest to said first detector and said second light detector is at a position substantially nearest to said first light source, and said third light source is at said location corresponding to a midpoint position between said first light source and said first light detector and said third light detector is at said location corresponding to a midpoint position between said second light source and said second light detector.

* * * * *